US010143566B2

(12) United States Patent
Hyder

(10) Patent No.: US 10,143,566 B2
(45) Date of Patent: Dec. 4, 2018

(54) EXPANDABLE CORPECTOMY SPINE IMPLANT

(71) Applicant: Life Spine, Inc., Huntley, IL (US)

(72) Inventor: Zeshan Hyder, Munster, IN (US)

(73) Assignee: Life Spine, Inc., Huntley, IL (US)

( * ) Notice: Subject to any disclaimer, the term of this patent is extended or adjusted under 35 U.S.C. 154(b) by 0 days.

(21) Appl. No.: 15/445,769

(22) Filed: Feb. 28, 2017

(65) Prior Publication Data
US 2017/0246010 A1    Aug. 31, 2017

Related U.S. Application Data

(60) Provisional application No. 62/300,876, filed on Feb. 28, 2016.

(51) Int. Cl.
*A61F 2/44* (2006.01)
*A61B 17/70* (2006.01)
*A61F 2/30* (2006.01)

(52) U.S. Cl.
CPC .............. *A61F 2/4465* (2013.01); *A61F 2/44* (2013.01); *A61F 2002/3055* (2013.01);
(Continued)

(58) Field of Classification Search
CPC .............. A61F 2/4465; A61F 2/44; A61F 2002/30433; A61F 2002/30517;
(Continued)

(56) References Cited

U.S. PATENT DOCUMENTS 5,236,460 A    8/1993    Barber
5,458,641 A    10/1995   Ramirez Jimenez
(Continued)

FOREIGN PATENT DOCUMENTS

FR    2929106    10/2009
GB    2 083 754   9/1981
(Continued)

OTHER PUBLICATIONS

Search Report for International Application No. PCT/US2017/020045, dated Jun. 6, 2017, 9 pages.

*Primary Examiner* — Pedro Philogene
*Assistant Examiner* — David C Comstock
(74) *Attorney, Agent, or Firm* — Foley & Lardner LLP

(57) ABSTRACT

A corpectomy implant comprises a height/length-adjustable (expandable) cage and plate. The plate is mounted to the cage once height of the cage has been set. The cage has a first component and a second component that is movable with respect to the first component in order to increase height of the cage. The first and second components have cooperating structure that provides discreet cage height increments. The first component has a superior end configured to grip a superior vertebral body, while the second component has an inferior end configured to grip an inferior vertebral body, the superior end attached to the superior end of the plate, and the inferior end attached to the inferior end of the plate. The plate has holes for anterior fixation of the plate to superior and inferior vertebral bodies. Plates of incremental sizes accommodate differing heights of the cage.

14 Claims, 2 Drawing Sheets

(52) U.S. Cl.
CPC ............ *A61F 2002/30433* (2013.01); *A61F 2002/30517* (2013.01); *A61F 2002/30528* (2013.01); *A61F 2002/4475* (2013.01); *A61F 2310/00017* (2013.01); *A61F 2310/00023* (2013.01)

(58) Field of Classification Search
CPC .... A61F 2002/30528; A61F 2002/3055; A61F 2002/4475; A61F 2310/00017; A61F 2310/00023
USPC .................... 623/17.11, 17.16; 606/246, 280
See application file for complete search history.

(56) References Cited

U.S. PATENT DOCUMENTS

| | | | | |
|---|---|---|---|---|
| 5,776,198 | A * | 7/1998 | Rabbe | A61B 17/70 606/247 |
| 5,916,267 | A * | 6/1999 | Tienboon | A61F 2/44 623/17.11 |
| 2002/0169508 | A1 | 11/2002 | Songer et al. | |
| 2006/0074490 | A1* | 4/2006 | Sweeney | A61F 2/44 623/17.15 |
| 2014/0277469 | A1 | 9/2014 | Baynham | |
| 2015/0005880 | A1 | 1/2015 | Popa et al. | |

FOREIGN PATENT DOCUMENTS

| | | |
|---|---|---|
| WO | WO 92/01428 | 2/1992 |
| WO | WO 2006/039387 | 4/2006 |
| WO | WO 2008/106912 | 9/2008 |

* cited by examiner

EXPANDABLE CORPECTOMY SPINE IMPLANT

CROSS-REFERENCE TO RELATED APPLICATIONS

This U.S. non-provisional patent application claims the benefit of and/or priority under 35 U.S.C. § 119(e) to U.S. provisional patent application Ser. No. 62/300,876 filed Feb. 28, 2016 titled "Expandable Corpectomy Spine Implant," the entire contents of which is specifically incorporated herein by reference.

FIELD OF THE INVENTION

The present invention relates to orthopedic implants for the spine and, particularly, to spine implants for corpectomy surgery.

BACKGROUND OF THE INVENTION

Many people contend with spine issues as a result of age, disease, and trauma, as well as congenital or acquired complications and conditions. While some of these issues can be alleviated without surgery, other issues respond better to surgery. In some cases, surgery may include installing an implant into the spine. If vertebral fusion is required, the spine implant along with bone graft or bone graft material may be used. In cases of significant spinal cord problems such as, but not limited to, multi-level spinal stenosis, the spine surgeon may recommend removal of the vertebral body as well as the disc spaces at either end to completely decompress the spinal cord and nerves. This procedure is known as a corpectomy. A corpectomy may be performed in association with some form of discectomy.

Because the vertebral body and possibly more has been removed in a corpectomy, it must be mechanically reconstructed in order to provide spinal stability. Vertebral fusion provides the necessary mechanical reconstruction. Vertebral fusion may be accomplished by using a strut or bone graft which is a piece of allograft or autograft bone that is shaped to be accommodated in the open spinal space sometimes along with anterior instrumentation to help hold the construct together, or with a manufactured component known as a cage along with bone graft material, typically from the patient's own removed vertebra. The allograft/autograft bone graft or cage holds the remaining vertebrae apart. During healing, the vertebrae grow together and fuse.

It is increasingly common to use cages rather than allograft or autograft bone since allograft or autograft bone must come from a donor or the patient. Cages made of titanium, stainless steel, or other biocompatible synthetic material have been designed. These cages, however, are deficient for various reasons.

It is therefore an object of the present invention to provide a corpectomy implant that overcomes the deficiencies of the prior art.

SUMMARY OF THE INVENTION

A corpectomy implant comprises a height-adjustable (expandable) cage and associated plate. The plate is mounted to the height adjustable cage once height of the cage has been set.

The cage has a first component and a second component that is movable with respect to the first component in order to increase height of the cage. The first and second components have cooperating structure that provides discreet height increments of the cage. In one form, the first component has a plurality of openings along its length while the second component has a resilient protrusion that is captured in an opening of the first component in order to set cage height as the second component is moved relative to the first component.

The first component has a superior end that is configured to grip a superior vertebral body, while the second component has an inferior end that is configured to grip an inferior vertebral body. The superior end includes a boss configured to receive a fastener for attachment to the superior end of the plate, while the inferior end includes a boss configured to receive a fastener for attachment to the inferior end of the plate.

The first component comprises a cylindrical body having a hollow interior, while the second component comprises a cylindrical body sized for reception in the hollow interior of the first component. Axial movement of the second component within the hollow interior of the first component provides height adjustment. The cooperating structures of the first and second components provide discreet incremental height adjustment and fixation of the cage.

The plate has holes on its superior and inferior ends that receive bone screws for anterior fixation of the plate to superior and inferior vertebral bodies. The plate attaches to the cage via superior and inferior screws that are received in the superior and inferior bosses of the first and second components. Multiple openings mid-plate and in the first and second components of the cage allow for bone graft insertion and visualization. Plates of incremental sizes accommodate differing heights of the cage.

Further aspects of the present invention will become apparent from consideration of the drawings and the following description of a form of the invention. A person skilled in the art will realize that other forms of the invention are possible and that the details of the invention can be modified in a number of respects without departing from the inventive concept. The following drawings and description are to be regarded as illustrative in nature and not restrictive.

BRIEF DESCRIPTION OF THE DRAWINGS

The features of the invention will be better understood by reference to the accompanying drawings which illustrate a form of the present invention, wherein.

DETAILED DESCRIPTION OF THE INVENTION

Figure 1:
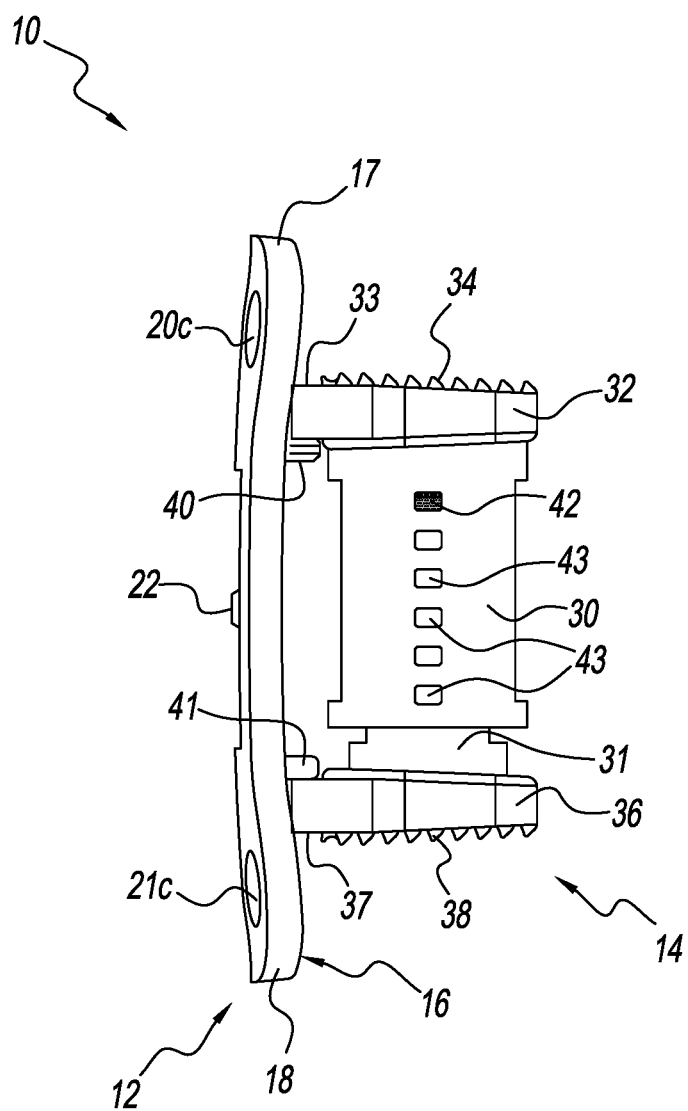
FIG. 1 is a side view of the present expandable corpectomy spine implant.
Figure 2:
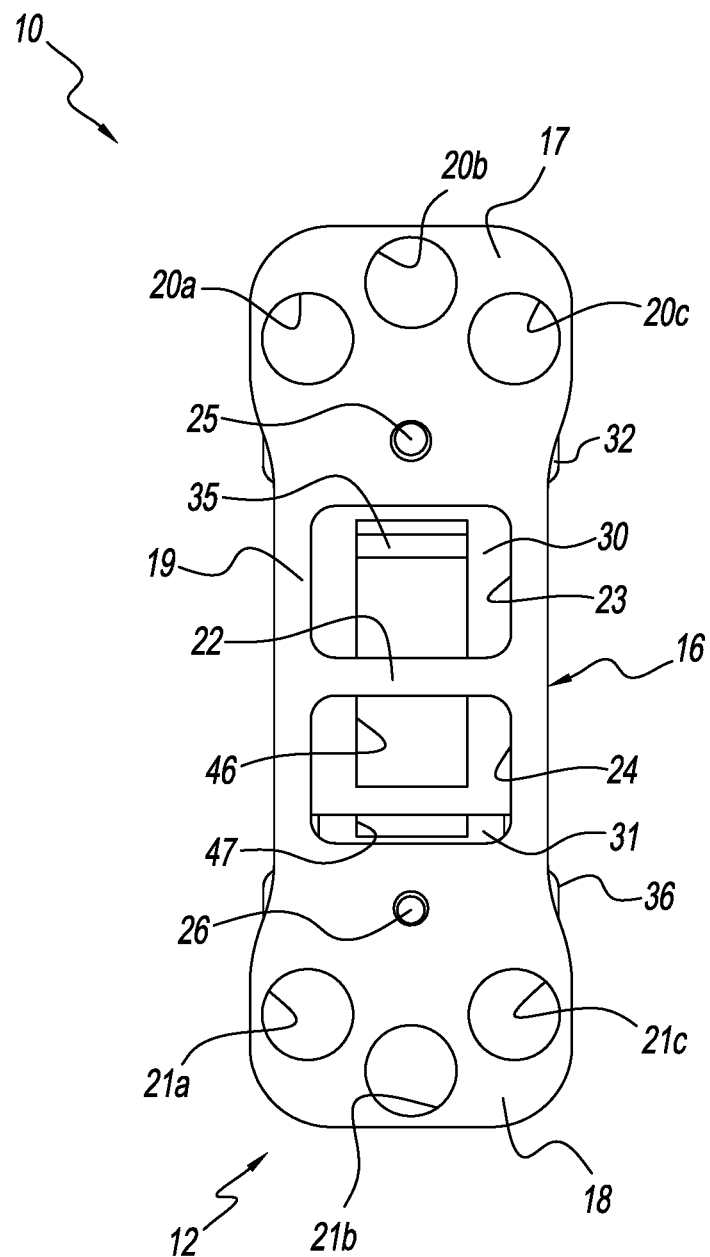
FIG. 2 is a rear view of the expandable corpectomy spine implant of FIG. 1.

Referring to the FIGS. 1 and 2, there is depicted an exemplary form of the present height-adjustable/expandable corpectomy spine implant, generally designated 10. The corpectomy spine implant 10 is made from a biocompatible material such as, but not limited to, titanium, stainless steel, an alloy of titanium or stainless steel, or otherwise. The corpectomy spine implant 10 is characterized by a spine plate (plate) 12 and a cage 14, the cage 14 composed of two components, namely, a first, superior, or outer component (collectively first component 30), and a second, inferior, or inner component (collectively, upper component 31), the nomenclature first and second being arbitrary. While the corpectomy spine implant 10 may be used, or adapted for use, between any two vertebrae of the spine, it is especially used for cervical vertebrae.

The plate 12 is defined by an elongated body 16 having a generally planar configuration with a slight superior/inferior and lateral curvature. The body 16 defines a superior end 17, an inferior end 18, and a middle section 19 between the superior and inferior ends 17, 18. The superior end 17 has three (3) holes 20a, 20b, 20c for receipt of bone screws (not shown) in order to attach the superior end 17 anteriorly to a superior vertebral body (not shown). More or less holes may be used. The inferior end 18 has three (3) holes 21a, 21b, 21c for receipt of bone screws (not shown) in order to attach the inferior end 18 anteriorly to an inferior vertebral body (not shown). More or less holes may be used. The body 16 further has an upper window 23 and a lower window 24 separated by a cross member 22 situated in the middle section 19. While two windows are shown, the plate 12 may have more or less windows as desired. Additionally, the plate has an upper bore 25 between the upper window 23 and the superior end 17, and a lower bore 26 between the lower window 24 and the inferior end 18. The upper and lower bores 25, 26 each accepts a fastener such as, but not limited to, a screw for affixing the cage 14 to the plate 12. Other configurations may be used.

In order to accommodate various heights of the cage 14, the plates 12 are provided in various lengths. The various lengths of the plates are dependent upon the length of height increments or extension of the cage 14. In the present form, the extension increments of the cage 14 are 1.5 mm and therefore, plates 12 are provided in incremental lengths differing by 1.5 mm. Since the upper and lower screw bores 25, 26 are in the same position for each plate, the upper and lower screw bores 25, 26 always align with the appropriate screw reception features of the cage as described below.

The first component 30 has a generally cylindrical body having a generally hollow interior and a head 32 on its superior end. The head 32 has an upper or superior surface 33 with a configuration 34 that is designed to grip a superior vertebral body (not shown). While the configuration 34 on the superior surface 33 is shown as a plurality of spikes or projections, other configurations may be used and are contemplated. While not seen, one or more openings may be provided in the head 32 that is in communication with the hollow interior of the cylindrical body to allow/promote bone fusion. The head 32 also carries a boss 40 that is configured to receive the fastener that attaches the first component 30 to the plate 12.

The first component 30 also includes a plurality of cutouts or openings 43 situated axially in and along the outside of the body from proximate the inferior end to proximate the superior end of the cylindrical first component 30. While each cutout 43 is shown as rectangular, other shapes may be used. The cutouts 43 are preferably, but not necessarily, equally spaced from one another to provide equal increments. As discussed further below, the cutouts 43 are part of the ratchet or expansion structure of the cage 14 that cooperates with ratchet or expansion structure of the second component 31 to provide expansion of the cage 14. As seen in FIG. 2, the first component 30 also has a window 46 which, along with the windows 23, 24 of the plate 12, provides communication with the interiors of the first and second components 30, 31 and allows for bone graft insertion and visualization. While only one (1) window 46 is shown, the first component 30 may have multiple windows if desired.

The second component 31 has a generally cylindrical body that is sized for reception in the hollow interior of the first component 30 having a preferably, but not necessarily, hollow interior and a head 36 on its inferior end. The head 36 has a lower or inferior surface 37 with a configuration 38 that is designed to grip an inferior vertebral body (not shown). While the configuration 38 on the inferior surface 37 is shown as a plurality of spikes or projections, other configurations may be used and are contemplated. While not seen, one or more openings may be provided in the head 36 that is in communication with the hollow interior of the cylindrical body to allow/promote bone fusion. The head 36 also carries a boss 41 that is configured to receive the fastener that attaches the second component 31 to the plate 12.

As seen in FIG. 2, the second component 31 has a window 47 which, along with the windows 23, 24 of the plate 12, provides communication with the interiors of the first and second components 30, 31, and allows for bone graft insertion and visualization. While only one (1) window 47 is shown, the second component 31 may have multiple windows if desired. The second component 31 also has another part of the of the ratchet or expansion structure of the cage 14 that cooperates with ratchet or expansion structure (i.e. cutouts 43) of the first component 31 to provide expansion of the cage 14. Such expansion is incremental and is controlled by the cooperating ratchet/expansion structures of the first and second components 30, 31. The cooperating ratchet/expansion structure of the second component 31 comprises a resilient, spring-loaded, or similar mechanism arm, pawl, or the like 42 whose protrusion is captured or retained in a cutout 43 of the first component 30 as the second component 31 axially moves in and relative to the first component 30. In FIG. 1, the arm 42 is captured in an upper-most cutout 43 thus providing a cage of least height. As the second component 31 is moved axially downwardly relative to the first component 30, the cage increases in height (expands). Expansion is accomplished in height increments determined by the distance between cutouts 43. If the arm 42 is captured in the lower-most cutout 43, the cage would be of greatest height.

After cage height is set, an appropriate sized plate 12 is attached to the cage 14 and to the superior and inferior vertebral bodies (not shown). In the corpectomy implant example shown in the figures, there would be six (6) plates corresponding to the six (6) increments/heights of the cage/cutouts.

It should be appreciated that dimensions of the components, structures, and/or features of the present expandable corpectomy implant may be altered as desired within the scope of the present disclosure. For example, the cooperating expansion structures could be detent and pin structures or the like.

What is claimed is:

1. A spine implant for use after a corpectomy, the spine implant comprising:
   a cage; and
   a bone plate;
   the cage having a first component defining an upper end and a first end opposite the upper end, and a second component defining a second end and a lower end opposite the second end, the second component received by the first component and movable in discreet increments with respect to the first component in order to effect a change in cage length, a first contact plate situated on the upper end of the first component and configured for contact with a first vertebral body, and a second contact plate situated on the lower end of the second component and configured for contact with a second vertebral body adjacent the first vertebral body, wherein the first component has a plurality of openings along its length; and the second component has a resilient protrusion that is capturable in one of the plurality of openings of the first component in order to set cage length as the second component is moved relative to the first component;

the bone plate having an upper portion, a lower portion, a plurality of upper screw bores situated in the upper portion for attaching the plate to an upper vertebral body, a plurality of lower screw bores situated in the lower portion for attaching the plate to a lower vertebral body adjacent the upper vertebral body, an upper boss for attachment to the first contact plate, and a lower boss for attachment to the second contact plate.

2. The spine implant of claim 1, wherein:
the first component comprises a hollow cylindrical body; and
the second component comprises a cylindrical body sized for reception in the hollow cylindrical body of the first component.

3. The spine implant of claim 2, further comprising:
a ratchet mechanism situated between the first component and the second component for effecting the discreet incremental movement.

4. The spine implant of claim 3, wherein the ratchet mechanism is configured to allow discreet 1.5 mm increments between the first component and the second component.

5. The spine implant of claim 2, further comprising:
first and second windows situated between the upper portion and the lower portion of the bone plate;
a first rear window situated in the hollow cylindrical body and aligning with the first and second windows of the bone plate; and
a second rear window situated in the cylindrical body and aligning with the first and second windows of the bone plate and the first rear window of the hollow cylindrical body.

6. The spine implant of claim 1, wherein:
the first contact plate has a plurality of upwardly extending protrusions; and
the second contact plate has a plurality of downwardly extending protrusions.

7. The spine implant of claim 6, wherein:
the plurality of upwardly extending protrusions comprise a plurality of first spikes; and
the plurality of downwardly extending protrusions comprise a plurality of second spikes.

8. A spine implant for use in corpectomy surgery, the spine implant comprising:
an interbody cage; and
a bone plate;
the interbody cage having a hollow component defining an upper end and a lower end opposite the upper end, and an interior component defining a top end and a bottom end opposite the top end, the interior component received in the hollow component and movable in discreet increments with respect to the hollow component in order to effect incremental expansion in length of the interbody cage, a first contact plate situated on the upper end of the hollow component and configured for contact with a first vertebral body, and a second contact plate situated on the bottom end of the interior component and configured for contact with a second vertebral body adjacent the first vertebral body, wherein the hollow component has a plurality of openings along its length; and the interior component has a resilient protrusion that is capturable in one of the plurality of openings of the hollow component in order to set cage length as the interior component is moved relative to the hollow component;

the bone plate having an upper portion, a lower portion, first and second windows situated between the upper portion and the lower portion, a plurality of upper screw bores situated in the upper portion for attaching the plate to the first vertebral body, a plurality of lower screw bores situated in the lower portion for attaching the plate to the second vertebral body adjacent the first vertebral body, an upper boss for attachment to the first contact plate, and a lower boss for attachment to the second contact plate.

9. The spine implant of claim 8, wherein:
the hollow component comprises a cylindrical body; and
the interior component comprises a cylindrical body sized for reception in the cylindrical body of the hollow component.

10. The spine implant of claim 9, further comprising:
a ratchet mechanism connected to the first component and the second component for effecting the discreet incremental movement.

11. The spine implant of claim 10, wherein the ratchet mechanism allows discreet 1.5 mm increments between the hollow component and the interior component.

12. The spine implant of claim 8, further comprising:
a first rear window situated in the hollow component and aligning with the first and second windows of the bone plate; and
a second rear window situated in the interior component and aligning with the first and second windows of the bone plate and the first rear window of the hollow first component.

13. The spine implant of claim 8, wherein:
the first contact plate has a plurality of upwardly extending protrusions; and
the second contact plate has a plurality of downwardly extending protrusions.

14. The spine implant of claim 13, wherein:
the plurality of upwardly extending protrusions comprise a plurality of first spikes; and
the plurality of downwardly extending protrusions comprise a plurality of second spikes.

* * * * *